(12) United States Patent
Zurflüh et al.

(10) Patent No.: US 6,451,855 B1
(45) Date of Patent: Sep. 17, 2002

(54) FUNGICIDAL COMBINATIONS COMPRISING GLYOXALIC ACID METHYL ESTER-O-METHYLOXIME DERIVATIVES

(75) Inventors: René Zurflüh, Bülach; Neil Leadbitter, Oberwil, both of (CH)

(73) Assignee: Bayer AKtiengesellschaft, Leverkusen (DE)

( * ) Notice: Subject to any disclaimer, the term of this patent is extended or adjusted under 35 U.S.C. 154(b) by 0 days.

(21) Appl. No.: 10/059,087

(22) Filed: Jan. 28, 2002

Related U.S. Application Data

(62) Division of application No. 09/728,185, filed on Dec. 2, 2000, now Pat. No. 6,395,761, which is a continuation of application No. PCT/EP99/03883, filed on Jun. 4, 1999.

(30) Foreign Application Priority Data

| Jun. 8, 1998 | (GB) | ............................................ 9812331 |
| Feb. 17, 1999 | (GB) | ............................................ 9903669 |

(51) Int. Cl.$^7$ ........................ A01N 37/12; A01N 37/44
(52) U.S. Cl. ........................................ 514/539; 514/617
(58) Field of Search ................................ 514/539, 617

(56) References Cited

U.S. PATENT DOCUMENTS

| 5,210,084 A | 5/1993 | Wollweber et al. ...... 514/237.5 |
| 5,342,837 A | 8/1994 | Clough et al. ............... 514/247 |
| 5,395,854 A | 3/1995 | Brand et al. .................. 514/619 |
| 5,407,902 A | 4/1995 | Oda et al. ..................... 504/336 |
| 5,411,987 A | 5/1995 | Wollweber et al. .......... 514/529 |
| 5,438,059 A | 8/1995 | Clough et al. ............... 514/256 |
| 5,491,165 A | 2/1996 | Dehne et al. ................. 514/479 |
| 5,516,786 A | 5/1996 | Wollweber et al. .......... 514/357 |
| 5,516,804 A | 5/1996 | Brand et al. .................. 514/619 |
| 5,523,454 A | 6/1996 | Brand et al. .................. 558/408 |
| 5,574,064 A | 11/1996 | Shibata et al. ............... 514/542 |
| 5,637,729 A | 6/1997 | Lacroix et al. ........... 548/316.7 |
| 5,677,347 A | 10/1997 | Brand et al. .................. 514/620 |
| 5,723,469 A | 3/1998 | Shibata et al. ............... 514/269 |
| 5,776,976 A | 7/1998 | Dehne et al. ................. 514/479 |
| 5,789,428 A | 8/1998 | Shibata et al. ............... 514/367 |
| 5,869,517 A | 2/1999 | Müller et al. ................. 514/407 |
| 5,889,059 A | 3/1999 | Bayer et al. .................. 514/619 |
| 5,906,986 A | 5/1999 | Latorse ......................... 514/141 |
| 6,002,016 A | 12/1999 | Lacroix et al. ........... 548/318.1 |
| 6,054,592 A | 4/2000 | Müller et al. ............. 548/371.1 |
| 6,057,363 A | 5/2000 | Dehne et al. ................. 514/479 |
| 6,075,042 A | 6/2000 | Latrose ......................... 514/376 |
| 6,100,263 A | 8/2000 | Bayer et al. .................. 514/241 |
| 6,187,812 B1 | 2/2001 | Bayer et al. .................. 514/522 |
| 6,191,128 B1 | 2/2001 | Stenzel et al. ............ 514/229.2 |
| 6,207,692 B1 | 3/2001 | Müller et al. ................. 514/384 |
| 6,245,772 B1 | 6/2001 | Dehne et al. ................. 514/269 |
| 6,303,598 B1 | 10/2001 | Stenzel et al. ............ 514/229.3 |

FOREIGN PATENT DOCUMENTS

| CA | 2043733 | 12/1991 |

*Primary Examiner*—Allen J. Robinson
(74) *Attorney, Agent, or Firm*—Joseph C. Gil; John E. Mrozinski, Jr.

(57) ABSTRACT

The present invention provides a method of combating phytopathogenic disease on a crop plant which comprises applying to the crop plant and/or its locus an effective amount of a combination of 2-[α-{[(α-methyl-3-trifluoromethyl-benzyl)imino]-oxy}-o-tolyl]-glyoxalic acid methyl ester-O methyloxime (I) and at least one compound selected from a broad variety of other plant fungicides. The combinations exhibit synergistic fungicidal activity and are particularly effective in combating or preventing diseases of crop plants.

3 Claims, No Drawings

FUNGICIDAL COMBINATIONS COMPRISING GLYOXALIC ACID METHYL ESTER-O-METHYLOXIME DERIVATIVES

This application is a divisional of U.S. application Ser. No. 09/728,185 filed Dec. 2, 2000, now U.S. Pat. No. 6,395,761 which is a continuation of international application PCT/EP99/03883 filed Jun. 4, 1999, the contents of which are fully incorporated by reference herein.

FIELD OF THE INVENTION

The present invention relates to novel fungicidal compositions for the treatment to phytopathogenic diseases of crop plants, especially phytopathogenic fungi, and to a method of combating phytopathogenic diseases on crop plants.

BACKGROUND OF THE INVENTION

It is known that certain strobilurin derivatives have biological activity against phytopathogenic fungi, e.g. from EP-A-460575 where their properties and methods of preparation are described. On the other hand anilide, carbamate and aminoacid amide fungicides are widely known as plant fungicides for application in various crops of cultivated plants. However, crop tolerance and activity against phytopathogenic plant fungi do not always satisfy the needs of agricultural practice in many incidents and aspects.

SUMMARY OF THE INVENTION

The present invention provides a method of combating phytopathogenic disease on a crop plant which comprises applying to the crop plant and/or its locus an effective amount of a combination of 2-[α-{[(α-methyl-3-trifluoromethyl-benzyl)imino]-oxy}-o-tolyl]-glyoxalic acid methyl ester-O-methyloxime (I) and at least one compound selected from a broad variety of other plant fungicides. The combinations exhibit synergistic fungicidal activity and are particularly effective in combating or preventing diseases of crop plants.

It has now been found that the use of a) 2-[α-{[(α-methyl-3-trifluoromethyl-benzyl)imino]-oxy}-o-tolyl]-glyoxalic acid methyl ester-O-methyloxime, compound I (EP-460575) in association with b) either a compound of formula IIA

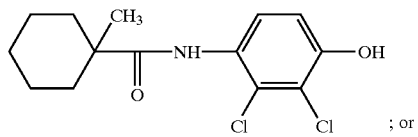
(IIA)

an anilide of formula IIB (EP-545099)

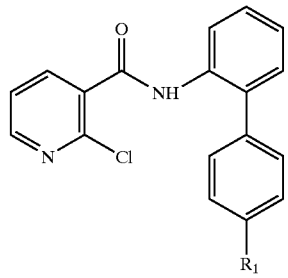
(IIB)

wherein $R_1$ is fluorine or chlorine; or a carbamate of formula IIC (WO-96/01256 and WO-96/01258)

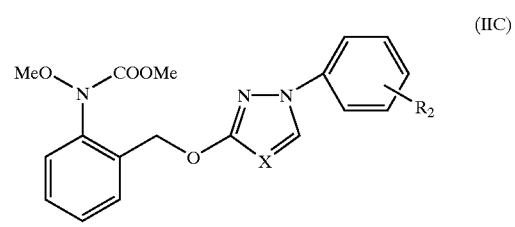
(IIC)

wherein X is N or CH, and $R_2$ is 4-$CH_3$, 4-Cl or 2,4-dichloro; or a compound IID (EP-278595)
methyl(2)-2-{2-[6-(trifluoromethyl)pyrid-2-yloxymethyl]-phenyl}-3-methoxyacrylate; or a compound IIE (EP-477631)
(E)-N-methyl-2-[2-(2,5-dimethyylphenoxymethyl)phenyl]-2-methoxy-iminoacetimide; or a compound of formula IIF (WO-95/21154)

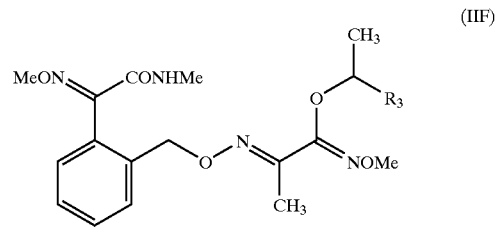
(IIF)

wherein $R_3$ is methyl or ethyl; or a (S)-valinamide of formula IIG (EP-398072, EP-610764, DE-4321897, WO-96/07638)

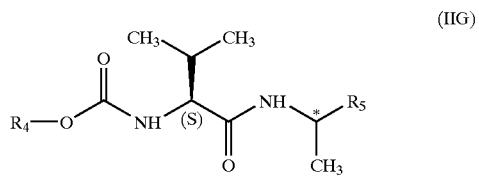
(IIG)

wherein $R_4$ is isopropyl, sec.-butyl or tert.-butyl, and $R_5$ is 4-chlorophenyl, 4-methylphenyl, 4-methoxyphenyl or β-naphthyl, and wherein the asymmetric center is preferably (R); or a (S)-valinamide of formula IIH (WO-94/25432, WO-96/04252)

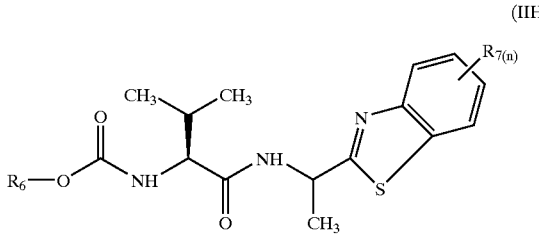

wherein $R_6$ is isopropyl, sec.-butyl or tert.-butyl, $R_7$ is halogen, methyl or methoxy and n is 0,1 or 2; or a compound IIJ (EP-596254)
N-methyl-2-[2-{α-methyl-3-(trifluoromethyl) benzyloximinomethyl}phenyl]-2-methoximinoacetamide; or a compound of formula IIK (EP-381330)

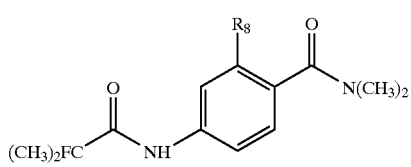

wherein $R_8$ is halogen or $C_1$–$C_4$-alkyl, preferably chlorine; or a compound IIL
N-(3'-(1'-chloro-3-methyl2'-oxopentan))-3,5-dichloro-4-methylbenzamide (EP-600629); or a compound IIM (EP-551048 and WO 96/03044)
(S)-1-anilino-4-methyl-2-methylthio-4-phenylimidazolin-5-one; or a compound of formula IIN (WO 98/25465)

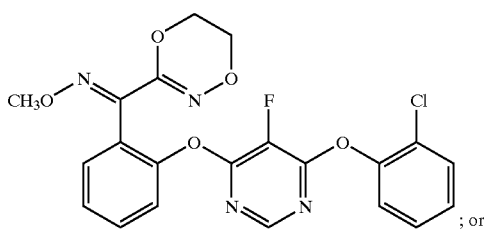

a compound of formula IIP (W098/20003)

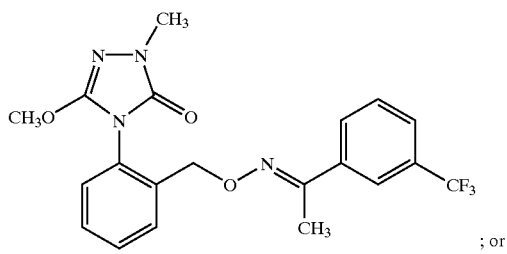

a compound IIQ
N-methyl-2-[α-{[(α-methyl-3-trifluoromethyl-benzyl) imino]-oxy}-o-tolyl]-glyoxalic acidamide-O-methyloxime (EP 569384)

is particularly effective in combating or preventing fungal diseases of crop plants. These combinations exhibit synergistic fungicidal activity.

The combinations according to the invention may also comprise more than one of the active components b), if broadening of the spectrum of disease control is desired.

The active ingredient combinations are effective against phytopathogenic fungi belonging to the following classes: Ascomycetes (e.g. Venturia, Podosphaera, Erysiphe, Monilinia, Mycosphaerella, Uncinula); Basidiomycetes (e.g. the genus Hemileia, Rhizoctonia, Puccinia); Fungi imperfecti (e.g. Botrytis, Helminthosporium, Rhynchosporium, Fusarium, Seotoria, Cercospora, Altemaria, Pyricularia and Pseudocercosporella herpotrichoides (Tapesia spp.)); Oomycetes (e.g. Phytophthora, Peronospora, Bremia, Pythium, Plasmopara).

Target crops for the areas of indication disclosed herein comprise within the scope of this invention e.g. the following species of plants: cereals (wheat, barley, rye, oats, rice, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, bananas and natural rubber plants, as well as ornamentals (flowers, shrubs, broad-leaved trees and evergreens, such as conifers). This list does not represent any limitation.

The combinations according to the present invention are particularly effective against Phytophthora, Peronospora, Bremia, Pythium and Plasmopara, in particular against pathogens of monocotyledoneous plants such as cereals, including wheat and barley.

The amount of combination of the invention to be applied, will depend on various factors such as the compound employed, the subject of the treatment (plant, soil, seed), the type of treatment (e.g. spraying, dusting, seed dressing), the purpose of the treatment (prophylactic or therapeutic), the type of fungi to be treated and the application time. Particularly preferred mixing partners of the compound I are those which comprise as component b) a compound IIB, IIG, IIH, IIK or IIL.

Another preferred mixing partners of the compound I are those which comprise as component b) a compound IIM, IIN, IIP or IIQ.

Another embodiment of the present invention is represented by those combination which comprise as component a) the compound I and as component b) a compound IIC, IID, IIE, IIF or IIJ.

Another combination is represented by the mixture comprising as component a) the compound I and as component b) the compound of the formula IIA.

It has been found that the use of compound I in combination with the compounds of formula II surprisingly and substantially enhances the effectiveness of the latter against fungi, and vice versa. Additionally, the method of the invention is effective against a wider spectrum of such fungi that can be combated with the active ingredients of this method when used solely. The weight ratio of a):b) is so selected as to give a synergistic fungicidal action. In general the weight ratio of a):b) is between 10:1 and 1:20. The synergistic action of the composition is apparent from the fact that the fungicidal action of the composition of a) +b) is greater than the sum of the fungicidal actions of a) and b).

Where the component b) is the compound IIA the weight ratio of a):b) is for example between 6:1 and 1:6, especially 2:1 and 1:2.

Where the component b) is a compound of formula IIB the weight ratio of a):b) is for example between 5:1 and 1:20, especially 2:1 and 1:20, and more preferably 1:1 to 1:10.

Where component b) is a compound of formula IIC, the weight ratio of a):b) is for example between 5:1 and 1:5, especially 3:1 and 1:3, and more preferably 2:1 and 1:2.

Where component b) is the compound IID, the weight ratio of a):b) is for example between 5:1 and 1:5, especially 3:1 and 1:3, and more preferably 2:1 and 1:2.

Where component b) is the compound IIE, the weight ratio of a):b) is for example between 5:1 and 1:5, especially 3:1 and 1:3, and more preferably 2:1 and 1:2.

Where component b) is a compound of formula IIF, the weight ratio of a):b) is for example between 5:1 and 1:5, especially 3:1 and 1:3, and more preferably 2:1 and 1:2.

Where component b) is a compound of formula IIG, the weight ratio of a):b) is for example between 5:1 and 1:5, especially 3:1 and 1:3, and more preferably 2:1 and 1:2.

Where component b) is a compound of formula IIH, the weight ratio of a):b) is for example between 5:1 and 1:5, especially 3:1 and 1:3, and more preferably 2:1 and 1:2.

Where component b) is the compound IIJ, the weight ratio of a):b) is for example between 5:1 and 1:5, especially 3:1 and 1:3, and more preferably 2:1 and 1:2.

Where component b) is a compound of formula IIK, the weight ratio of a):b) is for example between 5:1 and 1:20, especially 3:1 and 1:10, and preferably 2:1 and 1:5.

Where component b) is the compound IIl, the weight ratio of a):b) is for example between 5:1 and 1:5, specially 2:1 and 1:2, and more preferably 1.5:1 and 1:1.5.

Where component b) is the compound IIM, the weight ratio of a):b) is for example between 5:1 and 1:5, specially 2:1 and 1:2.

Where component b) is the compound IIN, the weight ratio of a):b) is for example between 6:1 and 1:6, specially 2:1 and 1:2.

Where component b) is the compound IIP, the weight ratio of a):b) is for example between 6:1 and 1:6, specially 2:1 and 1:2.

Where component b) is the compound IIQ, the weight ratio of a):b) is for example between 6:1 and 1:6, specially 2:1 and 1:2.

The method of the invention comprises applying to the treated plants or the locus thereof in admixture or separately, a fungicidally effective aggregate amount of compound I and a compound of component b).

The term locus as used herein is intended to embrace the fields on which the treated crop plants are growing, or where the seeds of cultivated plants are sown, or the place where the seed will be placed into the soil. The term seed is intended to embrace plant propagating material such as cuttings, seedlings, seeds, germinated or soaked seeds.

The novel combinations are extremely effective on a broad spectrum of phytopathogenic fungi, in particular from the Fungi imperfecti and Oomycetes classes. Some of them have a systemic action and can be used as foliar and soil fungicides.

The fungicidal combinations are of particular interest for controlling a large number of fungi in various crops or their seeds, especially wheat, rye, barley, oats, rice, maize, lawns, cotton, soybeans, coffee, sugarcane, fruit and ornamentals in horticulture and viticulture, and in vegetables such as cucumbers, beans and cucurbits.

The combinations are applied by treating the fungi or the seeds, plants or materials threatened by fungus attack, or the soil with a fungicidally effective amount of the active ingredients.

The agents may be applied before or after infection of the materials, plants or seeds by the fungi.

The novel combinations are particularly useful for controlling the following plant diseases:

Erysiphe graminis in cereals,

Erysiphe cichoracearum and Sphaerotheca fuliginea in cucurbits,

Podosphaera leucotricha in apples,

Uncinula necator in vines,

Puccinia species in cereals,

Rhizoctonia species in cotton, rice and lawns,

Ustilago species in cereals and sugarcane, Venturia inaequalis (scab) in apples, Helminthosporiumspecies in cereals, Septoria nodorum in wheat, Septoria tritici in wheat wheat, Rhynchosporium secalis on barley Botrytis cinerea (gray mold) in strawberries, tomatoes and grapes, Cercospora arachidicola in groundnuts, Peronospora tabacina on tobacco, Bremia lactucae on lettuce, Pythium debaryanum on sugar beet, Pseudocercosporella herpotrichoides (Tapesia spp.) in wheat and barley, Pyrenophera teres in barley Pyricularia oryzae in rice, Phytophthora infestans in potatoes and tomatoes, Fusarium and Verticillium species in various plants, Plasmopara viticola in grapes, Alternaria species in fruit and vegetables.

When applied to the plants the compound I is applied at a rate of 50 to 200 g/ha, particularly 75 to 150 g/ha, e.g. 75,100, or 125g/ha, in association with 50 to 1500 g/ha, particularly 60 to 1000 g/ha, e.g. 75 g/ha, 80 g/ha, 100 g/ha, 125 g/ha, 150 g/ha, 175 g/ha 200 g/ha, 300 g/ha, 500 g/ha, or 1000 g/ha of a compound of component b), depending on the class of chemical employed as component b). Where the component b) is the compound IIA for example 50 to 400 g a.i./ha is applied in association with the compound 1. Where the component b) is a compound of formula IIB for example 50 to 1500 g a.i./ha is applied in association with the compound 1. Where the component b) is a compound of formula IIC for example 50 to 300 g a.i./ha is applied in association with the compound 1. Where the component b) is the compound IID for example 50 to 300 g a.i./ha is applied in association with the compound 1. Where the component b) is the compound IIE for example 50 to 300 g a.i./ha is applied in association with the compound 1. Where the component b) is a compound of formula IIF for example 50 to 300 g a.i./ha is applied in association with the compound I. Where the component b) is a compound of formula IIG for example 50 to 400 g a.i./ha is applied in association with the compound 1. Where the component b) is a compound of formula IIH for example 50 to 400 g a.i./ha is applied in association with the compound I. Where the component b) is the compound IIJ for example 50 to 300 g a.i./ha is applied in association with the compound I. Where the component b) is a compound of formula IIK for example 20 to 2000 g a.i./ha is applied in association with the compound I. Where the component b) is the compound IIL for example 50 to 200 g a.i./ha is applied in association with the compound I. Where the component b) is the compound IIM for example 50 to 200 g a.i./ha is applied in association with the compound I. Where the component b) is the compound IIN for example 50 to 400 g a.i./ha is applied in association with the compound I. Where the component b) is the compound IIP for example 50 to 400 g a.i./ha is applied in association with the compound I. Where the component b) is the compound IIQ for example 50 to 400 g a.i./ha is applied in association with the compound I. In agricultural practice the application rates depend on the type of effect desired, and range from 0.02 to 3 kg of active ingredient per hectare.

When the active ingredients are used for treating seed, rates of 0.001 to 50, and preferably from 0.01 to 10 g per kg of seed are generally sufficient.

The invention also provides fungicidal compositions comprising the compound I and a compound of component b).

The composition of the invention may be employed in any conventional form, for example in the form of a twin pack, an instant granulate, a flowable or a wettable powder in combination with agriculturally acceptable adjuvants. Such compositions may be produced in conventional manner, e.g. by mixing the active ingredients with appropriate adjuvants (diluents or solvents and optionally other formulating ingredients such as surfactants). Suitable carriers and adjuvants may be solid or liquid and correspond to the substances ordinarily employed in formulation technology, such as, e.g. natural or regenerated mineral substances, solvents, dispersants, wetting agents, tackifiers, thickeners, binding agents or fertilizers. Such carriers are for example described in WO 96/22690.

Particularly formulations to be applied in spraying forms such as water dispersible concentrates or wettable powders may contain surfactants such as wetting and dispersing agents, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid adjuvant(s), the active agent consisting of at least the compound of formula I together with a compound of component b), and optionally other active agents, particularly guazatin and fenpiclonil. Concentrate forms of compositions generally contain in between about 2 and 80%, preferably between about 5 and 70% by weight of active agent. Application forms of formulation may for example contain from 0.01 to 20% by weight, preferably from 0.01 to 5% by weight of active agent.

Examples for specific formulations-combination are as disclosed e.g. in WO 96/22690, e.g. for wettable powders, emulsifiable concentrate, dusts, extruder granules, coated granules, suspension concentrate.

Slow Release Capsule Suspension 28 parts of a combination of the compound I and a compound of component b), or of each of these compounds separately, are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8–15 microns.

The resulting formulation is applied to seeds as an aqueous suspension in an apparatus suitable for that purpose.

Whereas commercial products will preferably be formulated as concentrates, the end user will normally employ dilute formulations.

BIOLOGICAL EXAMPLES

A synergistic effect exists whenever the action of an active ingredient combination is greater than the sum of the actions of the individual components.

The action to be expected E for a given active ingredient combination obeys the so-called COLBY formula and can be calculated as follows (COLBY, S.R. "Calculating synergistic and antagonistic responses of herbicide combination". Weeds, Vol. 15, pages 20–22; 1967):

ppm=milligrams of active ingredient (=a.i.) per litre of spray mixture X=% action by active ingredient I using p ppm of active ingredient Y=% action by active ingredient 11 using q ppm of active ingredient.

According to Colby, the expected (additive) action of active ingredients 1+11 using p+q ppm of active ingredient is $$E = X + Y - \frac{X \cdot Y}{100}$$

If the action actually observed (O) is greater than the expected action (E), then the action of the combination is superadditive, i.e. there is a synergistic effect.

Alternatively the synergistic action may also be determined from the dose response curves according to the so-called WADLEY method. With this method the efficacy of the a.i. is determined by comparing the degree of fungal attack on treated plants with that on untreated, similarly inoculated and incubated check plants. Each a.i. is tested at 4 to 5 concentrations. The dose response curves are used to establish the EC90 (i.e. concentration of a.i. providing 90% disease control) of the single compounds as well as of the combinations (EC $90_{observered}$). The thus experimentally found values of the mixtures at a given weight ratio are compared with the values that would have been found were only a complementary efficacy of the components was present (EC 90 $(A+B)_{expected}$). The EC90 $(A+B)_{expected}$ is calculated according to Wadley (Levi et al., EPPO- Bulletin 16, 1986, 651–657):

$$EC90(A+B)_{expected} = \frac{a+b}{\frac{a}{EC90(A)_{observed}} + \frac{b}{EC90(B)_{observed}}}$$

wherein a and b are the weight ratios of the compounds A and B in the mixture and the indexes (A), (B), (A+B) refer to the observed EC 90 values of the compounds A, B or the given combination A+B thereof. The ratio EC 90 $(A+B)_{expected}$/EC 90 $(A+B)_{observed}$ expresses the factor of interaction (F). In case of synergism, F is >1.

Example B-1
Residual-Protective action Against *Venturia inaegualis* on Apples Apple cuttings with 10–20 cm long fresh shoots are sprayed to drip point with an aqueous spray mixture prepared from a wettable powder formulation of the active ingredient mixture and infected 24 hours later with a conidia suspension of the fungus. The plants are incubated for 5 days at 90–100% relative humidity and stood in a greenhouse for a further 10 days at 20–24° C. Fungus infestation is evaluated 12 days after infection.

Example B-2(a)
Action Against *Botrytis cinerea* on Apple Fruits

Artificially damaged apples are treated by dropping a spray mixture of the active ingredient mixture onto the damage sites. The treated fruits are then inoculated with a spore suspension of the fungus and incubated for one week at high humidity and about 20° C. The fungicidal action of the test compound is derived from the number of damage sites that have begun to rot.

Example B-2(b)
Action Against *Botritis cinerea* on Tomatoes 4 week old tomato plants cv. "Roter Gnom" were treated with the formulated testcompound in a spray chamber. Two days after application the tomato plants were inoculated by spraying a spore suspension on the test plants. After an incubation period of 4 days at 20° C. and 95% relative humidity in a growth chamber the disease incidence was assessed.

Example B-2(c)
Action Against *Botritis cinerea* on Grapes 5 week old grape seedlings cv. "Gutedel" were treated with the formulated testcompound in a spray chamber. Two days after application the grape plants were inoculated by spraying a spore suspension on the test plants. After an incubation period of 4 days at 21° C. and 95% relative humidity in a greenhouse the disease incidence was assessed.

Example B-3
Action Against *Podosphaera leucotricha* on Apple Shoots

Apple cuttings with about 15 cm long fresh shoots are sprayed with a spray mixture of the active ingredient mixture. The treated plants are infected 24 hours later with a conidia suspension of the fungus and placed in a climatic chamber at 70% relative humidity and 20° C. Fungus infestation is evaluated 12 days after infection.

Example B-4
Action Against *Drechslera teres* on Barley 1 0-day-old barley plants of the "Golden Promise" variety are sprayed with a spray mixture of the active ingredient mixture. The treated plants are infected 24 hours later with a conidia suspension of the fungus and incubated in a climatic chamber at 70% relative humidity and 20–22° C. Fungus infestation is evaluated 5 days after infection.

Example B-5
Efficacy Against *Erysiphe graminis* f.SD. Tritici on Wheat

Five to ten wheat seeds c.v. "Arina" are sown in plastic pots of 7 cm diameter and grown for 7 to 12 days at 20 C., 50–70% rH. When the primary leaves have fully expanded, the plants are spray treated with aqueous spray liquors containing the single compounds, or mixtures thereof (hereinafter a.i.). All compounds are used as experimental or commercially available formulations, combinations are applied as tank mixtures. The application comprises foliar spraying to near runoff (three pots per treatment). 24 hours after the application or 24 hours before application, the plants are inoculated in a settling tower with fresh spores of *Erysiphe graminis* f. sp. tritici. The plants are then incubated in a growth chamber at 20° C., 60% rH. Seven days after the inoculation, the percentage of infection on primary leaves is evaluated. The efficacy of the a.i. is determined by comparing the degree of fungal attack on treated plants with that on untreated, similarly inoculated and incubated check plants. Each a.i. is tested at 4 to 5 concentrations. The synergy factor is calculated according to the COLBY method.

Example B-7
Activity Against *Uncinula necator*

Grape plants, 4 weeks old (4–5 leaves), are sprayed to near run off with a suspension containing 250 mg/l of active ingredient. The deposit is then allowed to dry. One day later, the treated plants are inoculated by dusting freshly harvested conidia over the test plants; then the plants were incubated in a growth chamber for 10–14 days at +22° C. and 70% r.h. The efficacy of the test compounds is determined by comparing the degree of fungal attack with that on untreated, similarly inoculated check plants. The mixtures according to the invention exhibit good activity in these Examples.

Example B-8

Activity Against *Plasmopara viticola* in Grapevines

Grapevine seedlings at the 4- to 5-leaf stage are sprayed to drip point with an aqueous spray mixture prepared with a wettable powder of the active ingredient mixture (0.02% of active ingredient) and, 24 hours later, infected with a sporangia suspension of the fungus. The fungus infestation is assessed 6 days after infection, during which time a relative atmospheric humidity of 95 to 100% and a temperature of 20° C. are maintained.

Example B-9
Activity Against *Phytophthora infestans* in Tomatoes a) Curative Action Tomato plants cv. "Roter Gnom" are grown for three weeks and then sprayed with a zoospore suspension of the fungus and incubated in a cabin at 18 to 20° C. and saturated atmospheric humidity. The humidification is interrupted after 24 hours. After the plants have dried, they are sprayed with a mixture which comprises the active ingredient formulated as a wettable powder at a concentration of 200 ppm. After the spray coating has dried, the plants are returned to the humid chamber for 4 days. Number and size of the typical foliar lesions which have appeared after this time are used as a scale for assessing the efficacy of the test substances.

b) Preventive-systemic Action

The active ingredient which is formulated as a wettable powder is introduced, at a concentration of 60 ppm (relative to the soil volume), onto the soil surface of three-week-old tomato plants cv. "Roter Gnom" in pots. After an interval of three days, the underside of the leaves is sprayed with a zoospore suspension of Phytophthora infestans. They are then kept for 5 days in a spray cabin at 18 to 20° C. and saturated atmospheric humidity. After this time, typical foliar lesions appear whose number and size are used for assessing the efficacy of the test substances.

Example B-10

Activity Against Phytophthora in Potato Plants a) Residual-protective Action

2–3 week old potato plants (Bintje variety) are grown for 3 weeks and then sprayed with a spray mixture (0.02% of active ingredient) prepared with a wettable powder of the active ingredient. After 24 hours, the treated plants are infected with a sporangia suspension of the fungus. The fungus infestation is assessed after the infected plants have been incubated for 5 days at a relative atmospheric humidity of 90–100% and 20° C.

b) Systemic Action

A spray mixture (0.002% of active ingredient based on the soil volume) prepared with a wettable powder of the active ingredient is poured next to 2–3 week old potato plants (Bintje variety) which have been grown for 3 weeks. Care is taken that the spray mixture does not come into contact with the aerial parts of the plants. After 48 hours, the treated plants are infected with a sporangia suspension of the fungus. Fungus infestation is assessed after the infected plants have been incubated for 5 days at a relative atmospheric humidity of 90–100% and 20° C.

The efficacy of the test combinations and the single active ingredients in the above tests is determined by comparing the degree of fungal attack with that on untreated, similarly inoculated check plants.

The mixtures according to the invention exhibit good activity in these Examples.

What is claimed is:

1. A method of combating phytopathogenic disease on a crop plant comprising applying to the crop plant and/or its locus a synergistic fungicidally effective amount of a combination comprising 2-[α-{[(α-methyl-3-trifluoromethyl-benzyl)imino]-oxy}-o-tolyl]-glyoxalic acid methyl ester-O-methyloxime (I), and N-(3'-(1'-chloro-3-methyl2'-oxopentan))-3,5-dichloro4-methylbenzamide (IIL).

2. A fungicidal composition comprising a synergistic fungicidally effective combination comprising 2-[α-{[(α-methyl-3-trifluoromethyl-benzyl)imino]-oxy}-o-tolyl]-glyoxalic acid methyl ester-O-methyloxime (I), and N-(3'-(1'-chloro-3-methyl 2'-oxopentan))-3,5-dichloro4-methylbenzamide (IIL).

3. The composition of claim 2 wherein the weight ratio of said 2-[α-{[(α-methyl-3-trifluoromethyl-benzyl)imino]-oxy}-o-tolyl]-glyoxalic acid methyl ester-O-methyloxime (I) and N-(3'-(1'-chloro-3-methyl2'-oxopentan))-3,5-dichloro4-methylbenzamide (IIL) is between 10:1 and 1:20.

* * * * *